(12) United States Patent
Lee et al.

(10) Patent No.: US 8,293,764 B2
(45) Date of Patent: *Oct. 23, 2012

(54) COMPOSITIONS AND METHODS FOR DISRUPTION OF BRCA2-RAD51 INTERACTION

(75) Inventors: Wen-Hwa Lee, Newport Coast, CA (US); Phang-Lang Chen, Irvine, CA (US); Jiewen Zhu, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 834 days.

This patent is subject to a terminal disclaimer.

(21) Appl. No.: 11/577,445

(22) PCT Filed: Oct. 19, 2005

(86) PCT No.: PCT/US2005/037513
§ 371 (c)(1),
(2), (4) Date: May 14, 2009

(87) PCT Pub. No.: WO2006/044933
PCT Pub. Date: Apr. 27, 2006

(65) Prior Publication Data
US 2009/0221634 A1 Sep. 3, 2009

Related U.S. Application Data

(60) Provisional application No. 60/620,496, filed on Oct. 19, 2004.

(51) Int. Cl.
*C07D 215/38* (2006.01)
*A61K 31/04* (2006.01)

(52) U.S. Cl. .......... 514/311; 514/313; 546/159
(58) Field of Classification Search .......... None
See application file for complete search history.

(56) References Cited

U.S. PATENT DOCUMENTS
6,306,426 B1 * 10/2001 Olejnik et al. .......... 424/426

OTHER PUBLICATIONS

Sidorenko et al., Synthesis and antimicrobial activity of sulfonyl derivatives of 1,2-dihydroisoquinolines and 1,2-dihydroquinolines, Khimiko-Farmatsevticheskii Zhurnal (1979), 13(7), 53-6.*
Casini et al., Sulfonamides and Sulfonylated Derivatives as Anticancer Agents, Current Cancer Drug Targets, 2002, 2, 55-55.*
Sidorenko, L. M., et al., "Synthesis and Antimicrobial Activity of Sulfonyl Derivatives of 1, 2-dihydroisoquinolines and -quinolines", Khimiko-Farmatsevticheskii Zhurnal, 13(7), 53-6 ISSN: 0023-1134, 1979.
Makarova L. YE., et al, "Influence of Oxidation Inhibitors on the Process of Food Fats Spoiling", lzvestiya Vysshikh Uchebnykh Zavedenit, vol. 1, 1992, pp. 34-36.
Pellegrini L et al., "Insights into DNA Recombination from the Structure of a Rad51-BRCA2 Complex", Nature, Nature Publishing Group, London GB, vol. 420, No. 6913, Nov. 21, 2002, p. 292, paragraph entitled "Implications".
Chen Phang-Lang et al., "The BRC Repreats in BRCA2 are Critical for Rad51 Binding and Resistance to Methyl Methanesulfonate Treatment", Proceedings of the National Academy of Sciences of the US, vol. 95, No. 9, Apr. 28, 1998, pp. 5287-5292.
Chen Chi-Fen et al., "Expression of Brc Repeats in Breast Cancer Cells Disrupts the BRCA2-Rad51 Complex and Leads to Radiation Hypersensitivity and Loss of G2/M Checkpoint Control", Journal of Biological Chemistry, vol. 274, No. 46, Nov. 12, 1999, pp. 32931-32935.

* cited by examiner

*Primary Examiner* — Shengjun Wang
*Assistant Examiner* — Svetlana M Ivanova
(74) *Attorney, Agent, or Firm* — Fish & Associates, PC

(57) ABSTRACT

Contemplated compounds disrupt interaction between BRCA2 and RAD51, likely by binding to RAD51. Based on the crucial role of the BRCA2-RAD51 complex formation in DNA repair and the role of RAD51 in the control of entry into S-phase from G1, numerous compositions and methods are presented. Among other advantageous uses, contemplated compounds may be employed as protective agents for non-neoplastic cells in chemotherapy before exposure of the cells to a chemotherapeutic drug, and/or as DNA-damage sensitizer for neoplastic cells.

8 Claims, 8 Drawing Sheets

COMPOSITIONS AND METHODS FOR DISRUPTION OF BRCA2-RAD51 INTERACTION

This application claims priority to our U.S. provisional patent application with the Ser. No. 60/620,496, filed Oct. 19, 2004, and which is incorporated by reference herein.

This invention was made with government support under grant number 44510-78004 and grant number DAMD 17-01-0409 from the Department of Defense. The government may have certain rights in the invention.

FIELD OF THE INVENTION

The field of the invention is compositions and methods related to DNA repair in mammals, and especially as they relate to RAD51 and BRCA2.

BACKGROUND OF THE INVENTION

DNA double-strand breaks are considered the principal lethal damage resulting from irradiation and/or exposure to cross-linking drugs (e.g., cisplatin, mitomycin, doxorubicin, bleomycin, etc.). Typically, double-strand breaks lead to arrest in the cell cycle progression and to activation of the cellular DNA repair machinery, and failure of DNA repair generally leads to genome abnormality, and eventually cell death.

Among other mechanisms, homologous recombination significantly contributes to the repair of DNA damage, and particularly double strand breaks. Several genes are involved in homologous recombination and include BRCA1, BRCA2, RAD51, RAD54, XRCC2, and XRCC3. Where these genes are mutated, cells will frequently exhibit high levels of genomic instability and hypersensitivity toward irradiation and/or crosslinking agents. On the other hand, in many cancer cells, and especially those that are genomically instable, elevated rates of homologous recombination have been observed. In these cancer cells, elevated expression levels of wild-type RAD51 have been observed, which appears to suggest that RAD51 (which is also involved in maintaining genomic stability) may also be responsible for the resistance of cancer cells to DNA-damaging radio- or chemotherapy.

RAD51 is a eukaryotic recombinase and is homologous to the *E. coli* RecA protein. RAD51 has ATP-dependent DNA binding activity, multimerizes to form a nucleoprotein filament on single-stranded DNA, and is reported to catalyze homologous DNA pairing and strand exchange reactions in vitro. After treating cells with irradiation and/or DNA damaging agents, dramatic amounts of RAD51-foci can be observed at the site of DNA damage, which may further include other proteins related to homologous recombination (e.g., BRCA1, Rad54, BLM, and RPA), and especially BRCA2.

BRCA2 was identified as a breast tumor suppressor based on various studies of familial breast cancer, and deficiency in BRCA2 is often characterized by cumulative chromosome abnormalities, including chromosomal breaks, aberrant mitotic exchanges, and aneuploidy. More recently it has been demonstrated that BRCA2 is also required for homology-directed repair of chromosomal breaks. Consistent with its involvement in DNA repair, mouse embryos lacking BRCA2 exhibit radiation hypersensitivity, which is also characteristic of mouse embryos lacking RAD51.

The potential role of BRCA2 in DNA repair was first revealed by identification of its interaction with RAD51. It has been shown that the six highly conserved BRC repeats are involved in the interaction between RAD51 and BRCA2, and that the interaction between the BRC repeats of BRCA2 and RAD51 is critical for cellular response to DNA damage caused by methyl methanesulfonate. Among other support, such criticality is reflected in the findings that radiation-induced RAD51 foci formation is diminished in BRCA2-deficient cells, and in cells in which the interaction between BRCA2 and RAD51 is disrupted using BRC peptides. Also, the RAD51-DNA binding ability is specifically abolished in vitro in the presence of excess BRC peptide, as well as the RAD51 nucleoprotein filament formation is disrupted.

Thus, while numerous data appear to highlight the significance of BRCA2/RAD51 interaction in DNA repair, effective strategies to selectively interfere with such interaction as a treatment modality for BRCA2-associated cancer are elusive. Therefore, there is still a need for compositions and methods to interfere with BRCA2/RAD51 interaction in DNA repair, and especially in the context of treatment and chemoprevention of neoplastic diseases.

SUMMARY OF THE INVENTION

The present invention is directed to compositions and methods in which a compound interferes, and most typically disrupts or prevents BRCA2/RAD51 interaction, and/or RAD51 multimerization. Typically, such interference will lead to increased sensitivity of neoplastic cells to DNA damage, and to a failure of non-neoplastic cells to proceed to S-phase from G1 phase.

In one aspect of the inventive subject matter, a pharmaceutical composition includes a pharmaceutically acceptable carrier and a compound according to Formula 1:

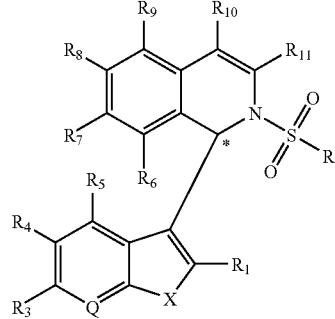

Formula 1 wherein R is a radical selected from the group consisting of an alkyl, alkenyl, alkynyl, cycloalkyl, cycloalkenyl, alkaryl, and

wherein Y is null or an alkylene group having 1 to 4 carbon atoms (and wherein R of Formula 1 is covalently bound to either the alkylene or, where Y is null, any atom of the ring that comprises Z); Q is N or C—$R_2$; Z is selected from —C($R_{12}$)=C($R_{13}$)—, —CH=N—, —N=CH—, O, S, or N$R_{14}$, where $R_{14}$ is H, alkyl, aryl, aralkyl, or acyl; X is selected from $CH_2$, O, S, or N$R_{14}$, where $R_{14}$ is independently as defined above; R' and $R_1$ through $R_{13}$ are independently selected from the group consisting of H, alkyl, alkenyl, alkynyl, cycloalkyl, cycloalkenyl, halo, nitro, hydroxy, alkoxy, alkenyloxy, cyano, carboxy, alkoxycarbonyl, carboxyalkyl, amino, acylamino, alkylamino, dialkylamino, cycloalkylamino, N-alkyl, N-cycloalkyl, amino, thio, alkylthio, and haloalkyl; with the proviso that $R_{12}$ and $R_{13}$ optionally combine to form a carbocyclic or heterocyclic ring; wherein n is between 0 and 4, inclusive, and wherein * denotes R or S configuration. More preferably, $R_1$, through $R_{11}$ are H, X is $NR_{14}$, and R is

In such compounds, it is especially preferred that Z is $—C(R_{12})\!\!=\!\!C(R_{13})—$, and Y is null. Therefore, particularly preferred compounds include those according to Formula 2 and Formula 3:

Formula 2

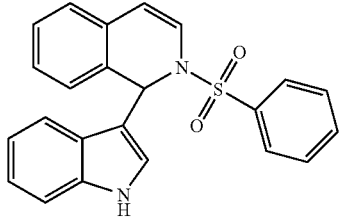

Formula 3

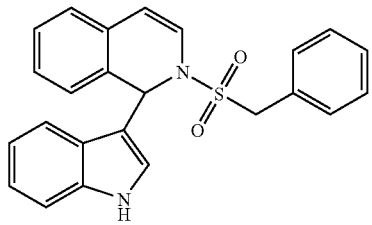

It is further contemplated that in such compositions the compound is present (a) at a concentration effective to increase sensitivity of a neoplastic cell to radiation and/or a DNA-damaging agent when the cell is exposed to the compound, or (b) at a concentration effective to reduce binding of BRCA2 to RAD51 when a BRCA2-RAD51 complex is exposed to the compound. Where desired, contemplated compositions may further include one or more DNA-damaging agents. Alternatively, it is also contemplated that the compound is present in the composition at a concentration effective to arrest a cell (most typically a non-neoplastic cell) in the G1 phase when the cell is contacted with the compound. In such cases, it is contemplated that the compound is coupled to an implanted device (e.g., endovascular stent) at a concentration effective to reduce cell proliferation of a plurality of cells proximal to the implanted device.

Therefore, in another aspect of the inventive subject matter, a method of treating a neoplastic cell is contemplated in which the neoplastic cell is contacted with contemplated compounds at a concentration effective (e.g., between 1 μM and 100 μM) to increase sensitivity of the neoplastic cell to radiation and/or DNA-damaging agents when the neoplastic cell is exposed to the compound. In further steps of such methods, the neoplastic cell may then be exposed to irradiation (e.g., gamma irradiation or UV-C irradiation) and/or DNA damaging agents (e.g., alkylating agent or crosslinking agent). Typically, preferred neoplastic cells include breast cancer cells and ovarian cancer cells.

In a still further aspect of the inventive subject matter, a method of arresting a non-neoplastic cell in G-phase will include a step in which the cell is contacted with contemplated compounds, a prodrug, or metabolite thereof, and wherein such compounds are present at a concentration effective to arrest the non-neoplastic cell in G-phase. Most preferably, such methods will further include a step of exposing the non-neoplastic cell to a DNA-damaging condition after the step of contacting, wherein the step of contacting is performed under conditions that reduce DNA damage of the cell as compared to a DNA damage that would be obtained without the step of contacting. As above, suitable DNA-damaging conditions are, among others, irradiation (e.g., gamma irradiation or UV-C) and/or exposure to DNA damaging agent (e.g., cis-platin, mitomycin, doxorubicin, melphalan, cyclophosphamide, chlorambucil, and bleomycin). Where desirable, the step of contacting the cell may also be performed such that the cell contacts an implanted device to which the compound is coupled.

Various objects, features, aspects and advantages of the present invention will become more apparent from the following detailed description of preferred embodiments of the invention.

DETAILED DESCRIPTION

Figure 1:
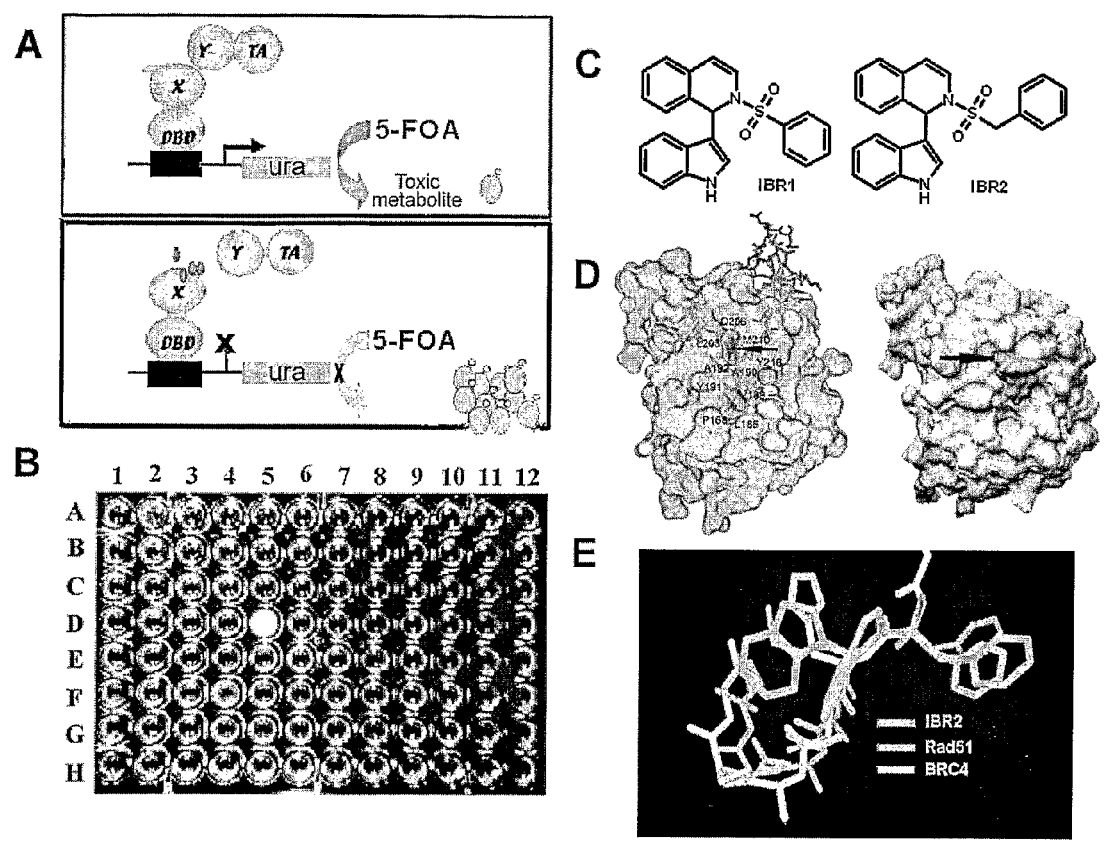
FIG. 1A is a schematic illustration of an exemplary reverse yeast two-hybrid screening system.
FIG. 1B is a photograph of a culture plate using the reverse yeast two-hybrid screening system of FIG. 1A.
FIG. 1C depict exemplary structures of selected compounds that were identified using the reverse yeast two-hybrid screening system.
FIG. 1D depicts a computer simulation of the BRC4-Rad51 complex on the left panel, and a computer simulation of the IBR2-Rad51 complex on the right panel.
FIG. 1E depicts a computer simulation of a structure alignment of IBR2 with BRC4 and RAD51 oligomerization motif.
FIG. 1F is a microphotograph depicting reduction of Rad51 foci in treated cells using contemplated compounds versus control.
FIG. 1G depicts exemplary structures of tested compounds and their activities in the yeast screening assay.

DNA damaging agents and radiation are among the most widely used therapies for late stage metastatic cancers, and are typically effective in eradicating at least a portion of the neoplastic cells. Unfortunately, neoplastic cells also use various mechanisms to repair the so induced DNA damage. Among other repair mechanisms, BRCA2-mediated repair has been implicated by the inventors in cancer resistance to DNA damaging agents and radiation.

BRCA2 binds to RAD51 through its BRC repeats, and this interaction appears to be critical for DNA repair. The inventors now contemplate that small molecules can be prepared to disrupt the interaction between BRC repeats and RAD51, to thereby reduce the effect or even eliminate one of the most essential error-free DNA repair machineries, and thus render cancer cells more sensitive to radiation or DNA-damaging chemotherapy.

A crystal structure of BRC4-RAD51 complex has recently been solved in which the BRC repeat mimics a RAD51 oligomerization motif. Thus, it was recently suggested that BRCA2 plays a controlling role for the RAD51-mediated homologous recombination. It was also known that BRCA2 contains three oligonucleotide-binding (OB) folds and a helix-turn-helix (HTH) motif. Based on these observations and other factors, the inventors contemplated that when DNA damage occurs, BRCA2 will recognize the ssDNA/dsDNA junction and the BRC repeats of the bound BRCA2 will then bring RAD51 to the damage sites, which then form a nucleoprotein filament on the ssDNA, leading to the formation of RAD51 foci, thus enabling subsequent homologous recombination processes. Consequently, the inventors contemplate that it would be desirable to develop molecules that interfere with (i.e., reduce), or even block BRCA2-RAD51 complex formation to thereby sensitize BRCA2-intact (non-mutated) breast cancer cells to the effects of radiation and other DNA damaging agents.

The inventors have now discovered that BRCA2-RAD51 complexes and/or complex formation can be disrupted or even completely inhibited by exposing the BRCA2-RAD51 complex to specific molecules and compositions comprising these molecules. Moreover, such molecules also demonstrated ability to interfere with RAD51 multimerization.

Therefore, it is generally contemplated that all processes and diseases associated with BRCA2-RAD51 complex formation and/or RAD51 multimerization can be modified by administration of such molecules. Among other contemplated processes and diseases, it is particularly contemplated that the compounds and compositions according to the inventive subject matter may be used to (a) sensitize neoplastic cells to the effects of chemotherapeutic drugs, (b) interfere with growth of neoplastic cells by disrupting cell division, (c) protect non-neoplastic cells from chemotherapeutic drug effects by arresting cells in G1 phase, and (d) reduce proliferation of (typically non-neoplastic) cells in an environment that would otherwise stimulate cell growth.

Contemplated Compounds and Compositions

It is generally contemplated that all molecules are suitable that prevent, reduce, or otherwise disturb formation or presence of a BRCA2-RAD51 complex. Therefore, and among numerous other molecules, peptides (e.g., BRC repeats and their analogs, antibody or other high-specificity/affinity binding peptide, etc) and small-molecule drugs (e.g., derived from a library of compounds as commercially available) and their derivatives, including prodrugs and metabolites are contemplated. However, particularly contemplated molecules include those according to Formula 1 below

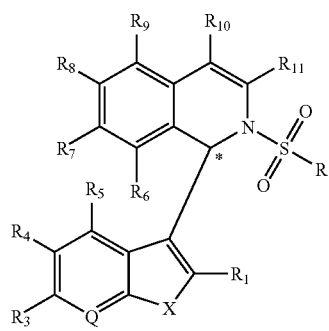

Formula 1 wherein R is a radical selected from the group consisting of an alkyl, alkenyl, alkynyl, cycloalkyl, cycloalkenyl, alkaryl (each of which may be substituted with $R_1$ and may further include a heteroatom such as N, S, O, Se, or O), and

wherein Y is null or an allylene group having 1 to 4 carbon atoms (and wherein R of Formula 1 is covalently bound to either the alkylene or, where Y is null, any atom of the ring that comprises Z); Q is N or C—$R_2$; Z is selected from —C($R_{12}$)=C($R_{13}$)—, —CH=N—, —N=CH—, O, S, or $NR_{14}$, where $R_{14}$ is H, or optionally substituted alkyl, aryl, aralkyl, or acyl; X is selected from $CH_2$, O, S, or $NR_{14}$, with $R_{14}$ independently as defined above; R', and $R_1$ through $R_{13}$ are independently optionally substituted and selected from the group consisting of H, alkyl, alkenyl, alkynyl, cycloalkyl, cycloalkenyl, halo, nitro, hydroxy, alkoxy, alkenyloxy, cyano, carboxy, alkoxycarbonyl, carboxyalkyl, amino, acylamino, alkylamino, dialkylamino, cycloalkylamino, N-alkyl, N-cycloalkyl, amino, thio, alkylthio, and haloalkyl; with the proviso that $R_{12}$ and $R_{13}$ optionally combine to form a carbocyclic or heterocyclic ring; wherein n is between 0 and 4, inclusive. Of course, it should be appreciated that all isomeric forms (e.g., diastereomers, enantiomers, tautomers, etc.) and mixtures thereof are contemplated. For example, where contemplated molecules have a chiral center (e.g., C* in Formula 1), both R and S configuration and a combination thereof are expressly contemplated herein. It should also be recognized that each of the aromatic ring systems in Formula 1 (the isoquinoline, indole, and benzene ring) may further include one or more heteroatoms, or may be further fused to another (optionally aromatic) ring system.

Still further preferred compounds will have a structure according to Formula 1 in which $R_1$ through $R_{11}$ are H, wherein X is $NR_{14}$, and wherein R is

and most preferably of those immediately above compounds in which Z is —C($R_{12}$)=C($R_{13}$)—, and Y is null. Therefore, particularly contemplated compounds include various substituted and unsubstituted phenylsulfonyl indolyl isoquinolines, and especially those having a structure according to Formulae 2 and 3 below Formula 2

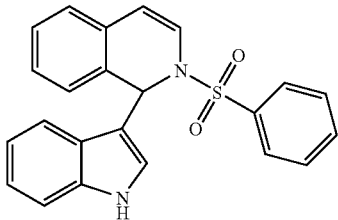

Formula 3

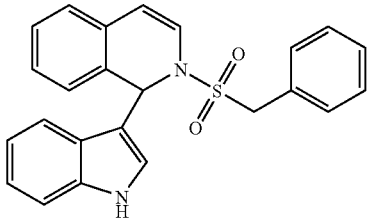

As used herein, the term "halogen" refers to a fluorine, bromine, chlorine, or iodine, which is typically covalently bound to another atom (e.g., carbon). As further used herein, the term "hydroxyl" refers to a-OH group. As still further used herein, the term "carbonyl atom" refers to a carbon atom to which three atoms are covalently bound, wherein one of the three atoms is bound to the carbon atom via a double bond (which may be partially delocalized). Thus, particularly contemplated carbonyl atoms include carbon atoms in a carboxamide group, a carboxamidine group, and a thiocarboxamide group.

The term "alkyl" as used herein refers to a cyclic, branched, or straight hydrocarbon in which all of the carbon-carbon bonds are single bonds, and the term "lower alkyl" refers to a cyclic, branched, or straight chain alkyl of one to ten carbon atoms (e.g., methyl, ethyl, n-propyl, i-propyl, n-butyl, t-butyl, i-butyl (or 2-methylpropyl), cyclopropylmethyl, i-amyl, n-amyl, hexyl, etc.). The term "alkylene" as used herein refers to an alkyl having two hydrogen atoms less than the corresponding alkane (i.e., $C_nH_{2n}$). For example, suitable alkylenes include methylene groups, ethylene groups, propylene groups, etc. The term "cycloalkyl" as used herein refers to a cyclic or polycyclic alkyl group containing 3 to 15 carbons. For polycyclic groups, these may be multiple condensed rings in which one of the distal rings may be aromatic (e.g., indanyl, tetrahydronaphthalene, etc.). The term "alkaryl" as used herein refer to an alky that is covalently coupled to an aryl moiety. For example, a benzyl radical is considered an alkaryl under the definition provided herein.

Similarly, the term "alkenyl" as used herein refers to an alkyl in which at least one carbon-carbon bond is a double bond. Thus, the term "lower alkenyl" includes all alkenyls with one to ten carbon atoms. The term "cycloalkenyl" as used herein refers to a cyclic or polycyclic group containing 3 to 15 carbons and at least one double bond. Likewise, the term "alkynyl" as used herein refers to an alkyl or alkenyl in which at least one carbon-carbon bond is a triple bond. Thus, the term "lower alkynyl" includes all alkynyls with one to ten carbon atoms.

As still further used herein, the term "alkoxy" refers to a-OR group, wherein R is lower alkyl, substituted lower alkyl, acyl, aryl, substituted aryl, arylalkyl, substituted arylalkyl, heteroarylalkyl, cycloalkyl, substituted cycloalkyl, cycloheteroalkyl, or substituted cycloheteroalkyl. Similarly, the term "aryloxy" refers to a-OAr group, wherein Ar is an aryl, substituted aryl, heteroaryl, or substituted heteroaryl group.

Furthermore, the term "aryl" refers to an aromatic carbocyclic group having at least one aromatic ring (e.g., phenyl or biphenyl) or multiple condensed rings in which at least one ring is aromatic, (e.g., 1,2,3,4-tetrahydronaphthyl, naphthyl, anthryl, or phenanthryl). The term "heteroatom" as used herein refers to an atom other than carbon (e.g., S, O, or N), which can optionally be substituted with, e.g., hydrogen, halogen, lower alkyl, alkoxy, lower alkylthio, trifluoromethyl, amino, amido, carboxyl, hydroxyl, aryl, aryloxy, heterocycle, heteroaryl, substituted heteroaryl, nitro, cyano, alkylthio, thiol, sulfamido and the like.

Still further, the term "substituted" as used herein means that a hydrogen atom that is covalently bound to a group or atom (or a free electron pair or electron pair of a double bond of an atom) is replaced by a covalently bound non-hydrogen substituent, including hydroxyl, thiol, alkylthiol, halogen, alkoxy, amino, amido, nitro, carboxyl, cycloalkyl, heterocycle, cycloheteroalkyl, acyl, carboxyl, aryl, aryloxy, heteroaryl, arylalkyl, heteroarylalkyl, alkyl, alkenyl, alknyl, and cyano.

The term "prodrug" as used herein refers to a modification of contemplated compounds, wherein the modified compound exhibits less pharmacological activity (as compared to the modified compound) and wherein the modified compound is converted within a target cell (e.g., neoplastic cell) or target organ (e.g., ovary) back into the modified form. For example, conversion of contemplated compounds into prodrugs may be useful where the active drug is too toxic for safe systemic administration, or where the contemplated compound is poorly absorbed by the digestive tract or other compartment or cell, or where the body breaks down the contemplated compound before reaching its target. Thus, it should be recognized that the compounds according to the inventive subject matter can be modified in numerous manners, and especially preferred modifications include those that improve one or more pharmacokinetic and/or pharmacodynamic parameter. For example, one or more substituents may be added or replaced to achieve a higher AUC in serum. On the other hand, and especially where increased solubility is desired, hydrophilic groups may be added. Exemplary suitable protocols for conversion of contemplated compounds into the corresponding prodrug form can be found in "Prodrugs (Drugs and the Pharmaceutical Sciences: a Series of Textbooks and Monographs)" by Kenneth B. Sloan (ISBN: 0824786297), and "Hydrolysis in Drug and Prodrug Metabolism: Chemistry, Biochemistry, and Enzymology" by Bernard Testa, Joachim M. Mayer (ISBN: 390639025X), both of which are incorporated by reference herein. Still further, and especially where contemplated compounds have a higher activity when the compound is metabolized (e.g., hydroxylated, glucuronidated, etc.), it should be appreciated that metabolites of contemplated compounds are also expressly contemplated herein.

Depending on the particular purpose, it should be recognized that contemplated compounds may be combined (in vivo or in a pharmaceutical formulation or administration regimen) with at least one other pharmaceutically active ingredient, and especially contemplated other ingredients include DNA damaging agents, cytostatic and/or cytotoxic drugs, antimetabolites, nucleoside analogs, etc. For example, suitable agents include alkylating agents and/or crosslinking agents such as cis-platin, mitomycin, doxorubicin, melphalan, cyclophosphamide, chlorambucil, and/or bleomycin. Concentrations of second pharmaceutically active ingredients are typically those recommended for stand-alone administration, however, lower (and in some cases higher) concentrations are also deemed suitable for use herein.

Therefore, contemplated pharmaceutical compositions will especially include those in which contemplated compounds (and additional pharmaceutically active ingredients) are provided with a suitable carrier, wherein contemplated compounds are preferably present at a concentration effective to increase sensitivity of a neoplastic cell to radiation (e.g., UV-C radiation and/or gamma radiation) or DNA-damaging agents (e.g., crosslinking or alkylating agent) when the cell is exposed to the compound. In further preferred compositions, it is also contemplated that the compound is present at a concentration effective to reduce or prevent binding of BRCA2 to RAD51 when BRCA2, RAD51, and/or a BRCA2-RAD51 complex is exposed to the compound. Where contemplated compositions are employed to at least temporarily arrest cells in a cell cycle, it is preferred that the compound is present at a concentration effective to arrest a (typically non-neoplastic) cell in the G1 phase when the cell is contacted with the compound. Thus, concentrations may be selected such that they are present at a concentration effective to reduce cell proliferation of cells (e.g., cells proximal to an implanted device to which the compounds are coupled, particularly including intimal cells proximal to an endovascular stent).

Depending on the particular use and structure, it is therefore contemplated that the compounds according to the inventive subject matter are present in the composition in an amount between 1 microgram to 1000 milligram, more typically between 10 microgram to 500 milligram, and most typically between 50 microgram to 500 milligram per single dosage unit. Thus, preferred concentrations of contemplated compounds in vivo or in vitro will generally be between 0.1 nM and 500 microM, more typically between 50 nM and 400 microM, and most typically between 100 nM and 200 microM.

Furthermore, it should be recognized that all formulations are deemed suitable for use herein and especially include oral and parenteral formulations. For example, for oral administration, contemplated compositions may be in the form of a tablet, capsule, suspension, or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compound that is administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. However, especially suitable quantities are provided above, and may therefore allow for a daily dose of about 0.001 (or even less) to 100 mg/kg body weight, preferably between about 0.01 and about 50 mg/kg body weight and most preferably from about 0.1 to 20 mg/kg body weight. Typically, a daily dose can be administered in one to four doses per day.

For therapeutic or prophylactic purposes, contemplated compounds are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Contemplated Uses

It is generally contemplated that the compounds and compositions according to the inventive subject matter may be employed to affect any condition and/or disease associated with BRCA2-RAD51 interactions. Therefore, particularly contemplated conditions and diseases include those in which it is desired to render cells sensitive to radiation and/or DNA damaging agents and/or in which cell division is dysregulated in response to a stimulus or transformation to a neoplastic phenotype. Additionally preferred conditions include those in which it is desirable to temporarily arrest cell growth.

For example, where contemplated compounds and compositions are particularly useful in chemotherapy where such compounds and compositions render neoplastic cells more sensitive to DNA damaging agents and/or radiation. Consequently, the dosage of chemotherapeutic agents in such treatments may be reduced and/or the kill rate increased. On the other hand, as contemplated compounds also arrest non-neoplastic cells in the G1 phase, it should be recognized that such compounds may be administered as a chemopreventative agent that temporarily arrests cell growth and thereby protects non-neoplastic cells from damage otherwise induced by a chemotherapeutic agent. Moreover, cell cycle arrest may also be utilized in implanted devices (e.g., endovascular stents) to reduce the occurrence and/or severity of restenosis. In such methods, it is contemplated that the compounds according to the inventive subject matter are coated onto the implanted device. Of course, numerous alternative manners of coupling such compounds in the implanted device are also deemed suitable and include covalent attachment to the scaffold or release portion that is coupled to the device, incorporation into a bioerodable or biodegradable material, etc.

Thus, and viewed from a molecular perspective, contemplated methods will employ compounds that interfere with BRCA2-Rad51 interaction as therapeutically active molecules to suppress radiation-induced RAD51 foci, promote cytostatic cell growth, provide synergetic induction of cell death when combined with cisplatin, and/or arrested such treated cells (and most typically cancer cells) at the G1 phase. As contemplated compounds may inhibit the binding of BRC repeat to RAD51, they may also be employed to prevent or reduce Rad51 multimerization, which ultimately will lead to the degradation of BRCA2 and RAD51. Therefore, suitable methods include all methods in which degradation of BRCA2 and RAD51 in a cell will produce a desirable result.

Syntheses of Exemplary Compounds

It should be appreciated that synthesis of numerous contemplated compounds will follow a general protocol as outlines below in which the compounds are prepared by direct reaction of three components of the compound. For example, suitable reactions will include (a) an optionally substituted and protected (where appropriate) isoquinoline, (b) an optionally substituted and protected (where appropriate) α-phenylmethylsulphonyl chloride or α-phenyl-sulphonyl chloride, and (c) an optionally substituted and protected (where appropriate) indole, wherein each of the components are combined as exemplarily outlined in Scheme 1 below.

EXAMPLE 1

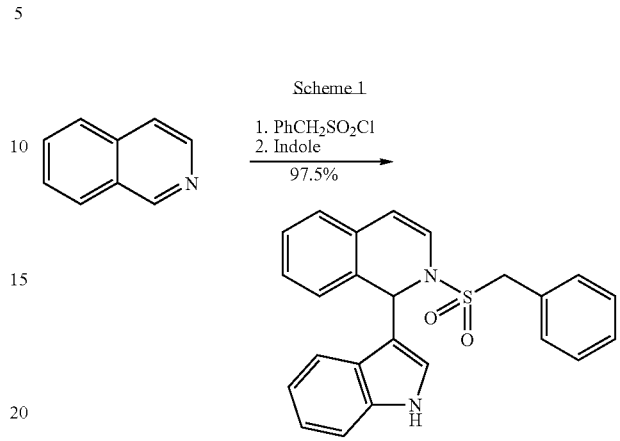

Scheme 1

2-(benzylsulfonyl)-1-(1H-indol-3-yl)-1,2-dihydroisoquinoline (IBR2): Isoquinoline (10.3 g, 80 mmol) was dissolved in anhydrous benzene (140 ml). α-phenylmethylsulphonyl chloride (7.64 g, 40 mmol) was added in portions. The reaction mixture was stirred at room temperature for 30 min. Indole (4.68 g, 40 mmol) was added and the reaction was continued at room temperature for 20 hr. During the reaction, a light-colored precipitation formed. Then the solid was collected and washed with toluene and hexane (50 ml each). The resulting crude product was further purified using flash chromatography (silica gel, 100% dichloromethane), yielding 11.1 g (97.5%) as a light yellow solid. The product (6.0 g) was further purified by recrystallization from ethanol (200 ml), to give a final product (5.7 g) as a white powder.

MS (m/e): 423.05 (M+Na$^+$). $^1$HNMR (500 MHz, δ/ppm): 4.00 (d, 1H, J=13.88 Hz), 4.16 (d, 1H, J=13.92 Hz), 6.06 (d, 1H, J=7.53 Hz), 6.30 (d, 1H, J=7.45 Hz), 6.37 (s, 1H), 6.70 (d, 1H, J=2.53 Hz), 6.86 (d, 1H, J=8.1 Hz), 6.91 (d, 2H, J=7.78 Hz), 7.08 (t, 2H, J=7.76 Hz), 7.13-7.32 (m, 7H), 7.96 (d, 1H, J=9.02 Hz), 8.00 (s, br, 1H).

EXAMPLE 2

Following the procedure of Example 1, 0.25 mmole of the optionally substituted indole was treated with 0.5 mmole of an optionally substituted isoquinoline and 0.25 mmol of α-phenylmethylsulphonyl chloride to yield substituted 2(benzylsulfonyl)-1-(1H-indol-3-yl)-1,2-dihydroisoquinolines, which are shown in the table immediately below (yields were derived from a single experiment and were not optimized).

| R | R1 | R2 | R3 | R4 | R5 | R6 | R7 | R8 | R9 | R10 | R11 | R14 | mg | % Yield |
|---|---|---|---|---|---|---|---|---|---|---|---|---|---|---|
| Benzyl | H | H | H | OMe | H | H | H | H | H | H | H | H | 34.81 | 33 |
| Benzyl | H | Br | H | H | H | H | H | H | H | H | H | H | 37.68 | 32 |
| Benzyl | H | H | H | H | Br | H | H | H | H | H | H | H | 91.85 | 78 |
| Benzyl | H | H | H | COOMe | H | H | H | H | H | H | H | H | 30.38 | 27 |
| Benzyl | H | H | H | NH2 | H | H | H | H | H | H | H | H | 55.96 | 55 |
| Benzyl | H | H | H | Br | H | H | H | H | H | H | H | H | 32.97 | 28 |
| Benzyl | H | H | H | H | H | H | H | H | H | H | H | Me | 73.08 | 72 |
| Benzyl | H | H | H | NHAc | H | H | H | H | H | H | H | H | 30.31 | 27 |
| Benzyl | H | H | H | NHCOPh | H | H | H | H | H | H | H | H | 63.88 | 50 |
| Benzyl | COOEt | H | H | H | H | H | H | H | H | H | H | H | 35.96 | 31 |

-continued

| R | R1 | R2 | R3 | R4 | R5 | R6 | R7 | R8 | R9 | R10 | R11 | R14 | mg | % Yield |
|---|----|----|----|----|----|----|----|----|----|-----|-----|-----|-----|---------|
| Benzyl | H | H | H | H | H | H | H | H | H | Br | H | H | 37.68 | 32 |
| Benzyl | H | H | H | H | Br | H | H | H | H | Br | H | H | 77 | 56 |
| Benzyl | H | H | H | Br | H | H | H | H | H | Br | H | H | 38.5 | 28 |
| Benzyl | H | H | H | OMe | H | H | H | H | H | Br | H | H | 35.07 | 28 |
| Benzyl | H | H | H | COOMe | H | H | H | H | H | Br | H | H | 33.06 | 25 |

EXAMPLE 3

2(benzylsulfonyl)-1-(7-aza-1H-indol-3-yl)-1,2-dihydroisoquinoline: Following the procedure of Example 1, 29.54 mg (0.25 mmol) of 7-azaindole was treated with 64.58 mg (0.5 mmole) of isoquinoline and 47.67 mg (0.25 mmol) of α-phenylmethylsulphonyl chloride to yield 58.95 mg (60% Yield) of 2(benzylsulfonyl)-1-(7-aza-1H-indol-3-yl)-1,2-dihydroisoquinoline.

EXAMPLE 4

2(benzylsulfonyl-1-(7-aza-1H-indol-3-yl)-4-bromo-1,2-dihydroisoquinoline: Following the procedure of Example 1, 29.54 mg (0.25 mmol) of 7-azaindole was treated with 104.03 mg (0.5 mmole) of 4-bromoisoquinoline and 47.67 mg (0.25 mmol) of α-phenylmethylsulphonyl chloride to yield 71.98 mg (61% Yield) of 2(benzylsulfonyl)-1-(7-aza-1H-indol-3-yl)-4-bromo-1,2-dihydroisoquinoline.

Experiments

Identification of Compounds that Interfere with the BRCA2-RAD51 Complex

Figure 1F:
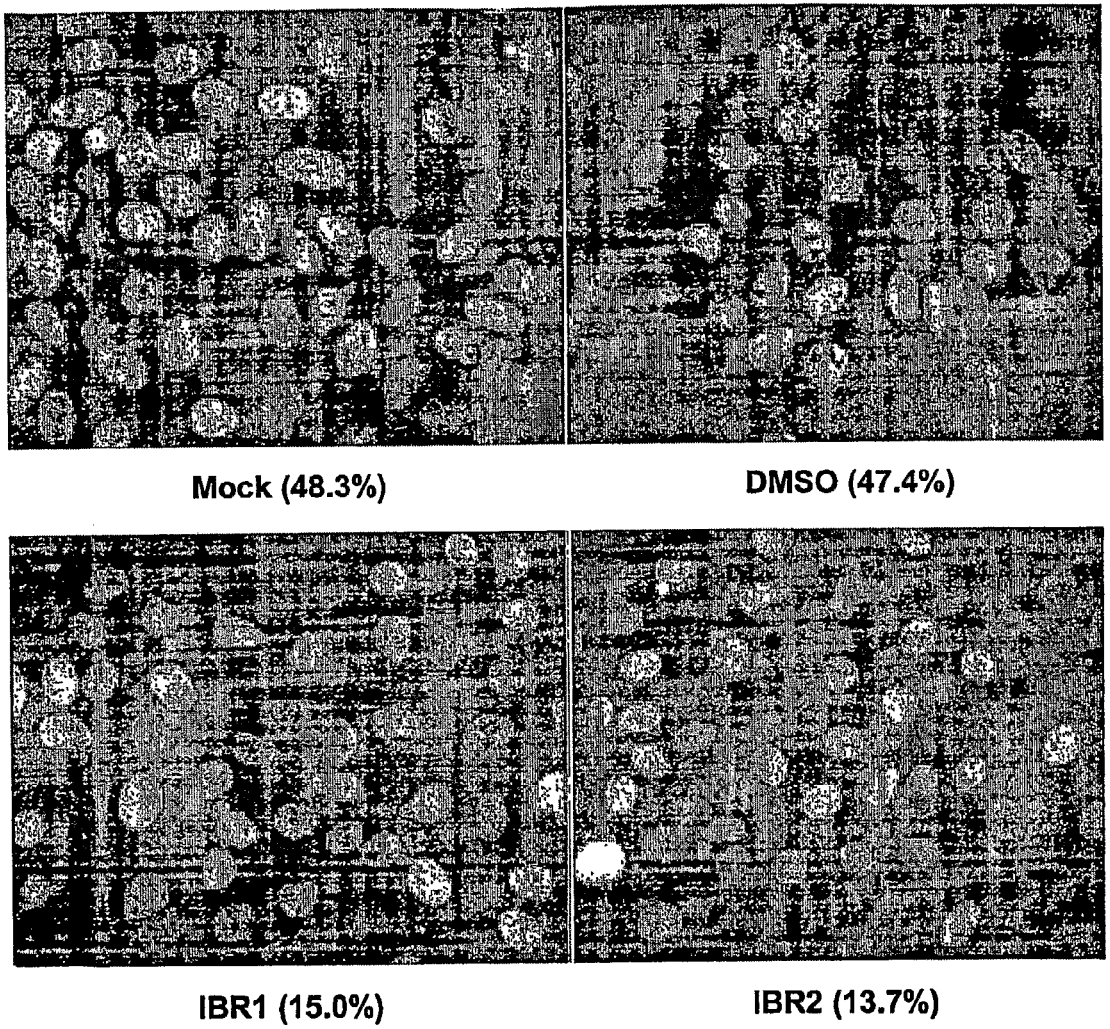

To identify compounds that could inhibit BRC-Rad51 interaction, a library of 24,000 synthetic compounds (Nanoscale Combinatorial Synthesis, Inc. Palo Alto, Calif.) was screened by an inducible reverse yeast two-hybrid method (Proc Natl Acad Sci USA 94, 13396-13401), which is schematically depicted in FIG. 1A. Two fusion proteins, TetR-BRC fusion protein (TetR/NCB, constitutively expressed), and Rad51-activation domain fusion protein (AD/Rad51 expressed under the GAL1 promoter), worked together as a transcriptional activator in a yeast strain harboring a TetOp-driven URA3 gene (Proc Natl Acad Sci USA 94, 12473-12478). The interaction between these two fusion proteins induced the expression of URA3 gene; then, a toxic metabolite from 5-FOA in the medium caused cell death (Methods Enzymol 154, 164-175). If the small molecules tested inhibited TetR/BRC/AD/Rad51 interaction, URA3 expression was abolished and cells were allowed to grow. An example of a positive hit from the reverse yeast two-hybrid screening is shown in FIG. 1B. While screening the library, sixteen compounds were found to promote yeast growth at concentrations below 10 µM. These compounds were then tested for their effects on IR-induced Rad51 foci formation in MCF-7 breast cancer cells. Two compounds (IBR1 and IBR2, structures depicted in FIG. 1C) dramatically reduced Rad51 foci formation (FIG. 1F) and were chosen for further investigation. Particularly, IBR2, which had a slightly stronger activity than IBR1, was studied in the majority of the experiments conducted in this paper.

Figure 1G:
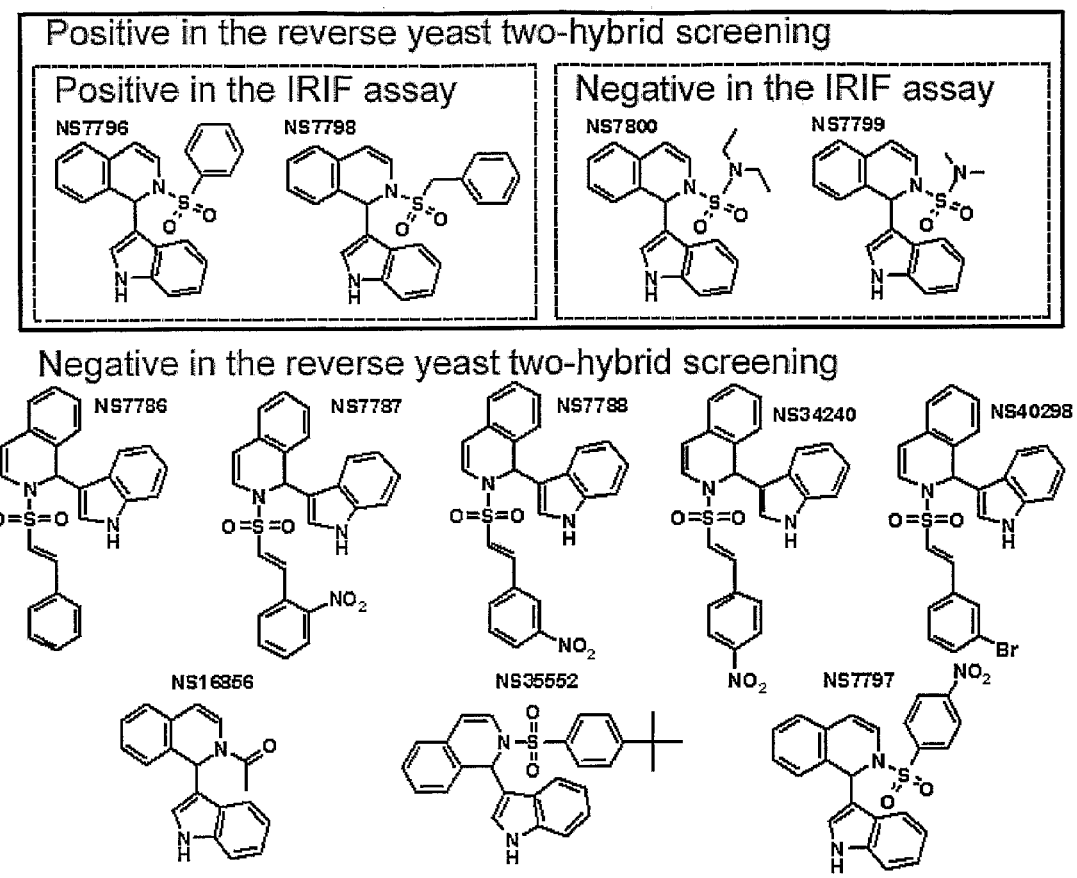

Remarkably, IBR1 and IBR2 are similar in molecular structure. They both comprise three aromatic rings, an isoquinoline, an indole, and a benzene ring, which make the compounds very hydrophobic in nature. The only difference between these two compounds lies in a methylene group that connecting the benzene ring to the core structure. The structural similarity suggests that these compounds may share similar mechanisms in their functioning. Interestingly, replacement of the benzene ring with other groups failed in disrupting RAD51/BRC interaction, as disclosed by reverse yeast two-hybrid screening of some of the IBR compound analogues, which may suggest the benzene ring took a role in binding with its target. In the initial screening, it was also found that other IBR analogues with larger substituents on the phenyl ring failed to disrupt BRC/Rad51 interaction. FIG. 1G depicts exemplary structures of selected tested compounds. These and other results suggest that the phenyl ring may play a role in the target binding. IBR analogues with substituents on the N-position of the indole ring also lost their activity in clonogenic assay (data not shown), suggesting a possible binding role of the NH group, probably through hydrogen bonding.

Investigation of Mechanism of Binding

The BRC repeats have a highly conserved hairpin structure, (e.g. 1524-FHTASGK-1530 in BRC4), which is involved in binding with RAD51. The BRCA2 sequence 1524-FHTA-1527 interacts with B3 of RAD51 through anti-parallel beta-stand paring; similar binding pattern was also observed in Rad51 filament formation. Importantly, both the F1524 of BRC4 in the BRC4-RAD51 complex or F86 of human RAD51 (equivalent to F144 in yeast Rad51 or F97 in *P. furiosus* Rad51) can reach deeply into the hydrophobic pocket in between B3 and A4, formed by M210, M158, A207, A190, A192, Q206, L203 and I160 of RAD51. Careful alignment of IBR2 structure with BRC4 hairpin structure and Rad51 oligomerization motif suggests the phenyl ring may mimic the F1524 of BRC4, while the remaining ring systems take the place of the adjacent beta strand. Molecular docking of IBR2 with RAD51 also suggests that IBR2 binds with RAD51 by extending its benzene group into the same binding pocket for BRCA2 binding or oligomerization (see FIGS. 1D and 1E). Based on the observation that the benzene ring of IBR compounds appears to be essential for their effectiveness, the inventors further hypothesized that one possibility of the IBR1/2 action mechanism is by mimicking the F1524 of BRCA2 and blocking the entrance of the hydrophobic binding pocket for F1524, therefore cause the failure of BRCA2/RAD51 docking.

Investigation of Binding Target

Figure 2:
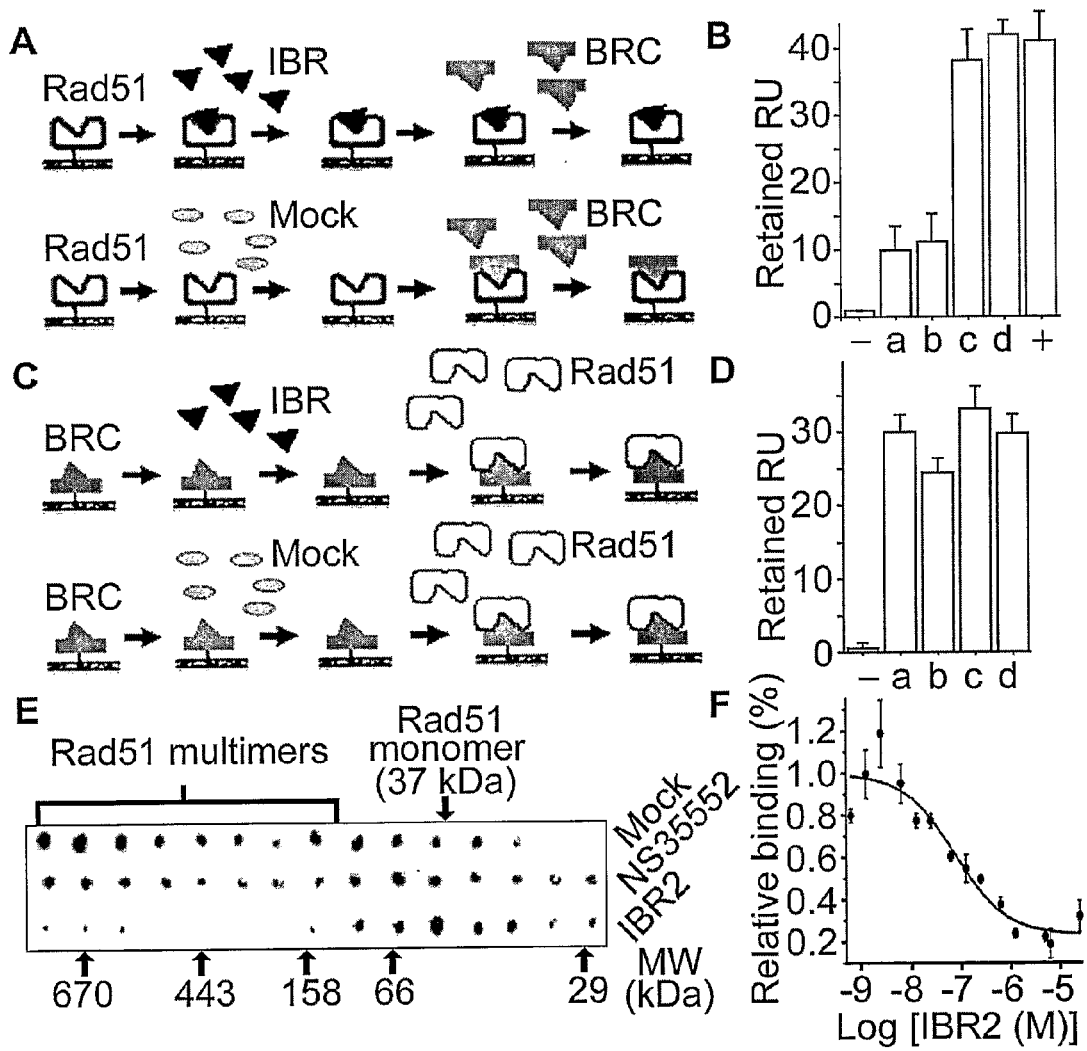
FIGS. 2A and 2C are schematic illustrations of surface plasmon resonance (SPR) experiments to determine the binding partner of IBR2.
FIGS. 2B and 2D are graphs depicting results of selected surface plasmon resonance experiments.
FIG. 2E is a dot-blot analysis of IBR2-mediated dissociation of Rad51 multimers as analyzed by gel filtration.
FIG. 2F is a graph depicting inhibition of Rad51-BRC1 repeat binding using SPR in a solution competition format for $IC_{50}$ determination.

The inventors then investigated if contemplated compounds bind to Rad51, but not BRCA2. To this end, surface plasmon resonance (SPR) was employed to directly determine whether Rad51 or the BRC repeat binds the small compounds. Instead of detecting the binding of small molecules directly, which would yield a very weak signal, an alternative method was used to detect the inhibition of protein binding. Briefly, one of the proteins was attached to the sensor chip, and IBR compounds were allowed to pass through the surface. Then, the binding of the second protein was measured. If IBR compounds bind to the immobilized protein, the binding of the second protein will be reduced, which is schematically depicted in FIGS. 2A and 2C. As shown in FIGS. 2B and 2D, upon IBR compound pretreatment, the immobilized Rad51 lost the ability to bind BRC repeat (FIG. 2B), while the compound pretreatment did not affect the binding of the immobilized BRC repeat to Rad51 (FIG. 2D). These results indicate that IBR compounds bind Rad51, rather than BRC repeat.

If the IBR compound indeed occupies the hydrophobic pocket for the entrance of Phe1524 in BRCA2, the oligomerization of Rad51 should also be affected since they share the same binding region. Previous studies showed that the BRC repeat can cause the dissociation of Rad51 multimers. Therefore, if IBR2 mimics the BRC hairpin structure, the Rad51 multimerization will also be inhibited by IBR2. We compared the gel filtration profile of Rad51 between with and without IBR2. Rad51 exhibited a broad elution profile indicative of the presence of multimeric and monomeric species, as previously described. However, in the presence of IBR2, the Rad51 elution profile exhibited a major peak consistent with the molecular weight of a monomer as depicted in FIG. 2E. These results indicate that IBR2, like the BRC repeats, dissociates Rad51 multimers. The inhibition of the Rad51 and BRC repeat binding was further analyzed by SPR technology in a solution competition format as previously described (see e.g., Science 303, 844-848). As can be seen from FIG. 2F, the IBR2 compound displaced the BRC repeat from the complex with Rad51 with median inhibitory concentration (IC50) value of about 115 nM.

Based on the above observations, the inventors contemplate that if the phenyl ring of IBR compounds indeed mimics the Phe1524 of BRC4 repeat and reaches the binding pocket, an appropriate size of the phenyl moiety must be critical for the activity. Such hypothesis was supported by various experiments in which it was found that when the phenyl ring is absent (NS16856) or the linker between isoquinoline and benzene rings is too long (NS7786, NS7787, NS7788, NS34240, and NS40298), the activities of these compounds are negligible in the reverse yeast two-hybrid assay (see FIG. 1G). the inventors further examined an IBR2 analogue (NS35552) with a large substituent (tert-butyl) at para-position of the phenyl ring, which already showed negative result in reverse yeast two-hybrid assay. In the presence of NS35552, Rad51 was still able to form multimers as shown in FIG. 2E, further suggesting that the size of the phenyl ring structure on contemplated compounds is critical to at least some degree for their effect.

The inventors therefore contemplate that the mechanism of contemplated compounds is based to at least some extent on hydrophobic interaction with the same binding pocket on Rad51 core domain to prevent the binding of BRC repeats as well as to disrupt Rad51 multimer formation.

Biological Effects of Contemplated Compounds on Various Cells and Animal Models Among various other biological effects (data not shown), contemplated compounds, and particularly IBR2 retarded growth of breast tumor cells in culture and significantly reduced tumorigenicity in nude mice. Moreover, cancer cells treated with contemplated compounds exhibited arrest at G1 phase and defect in mitotic entry. This also correlated with the accelerated degradation of Rad51 via the proteasome pathway. Contemplated compounds further augmented cytotoxic activity of selected chemotherapeutic agents, including VP-16, taxol, camptothecin, and ionizing irradiation upon treatment of tumor cells. Based on the below data and other considerations, the inventors therefore contemplate that the compounds according to the inventive subject matter are suitable for targeting the interaction between BRCA2 and Rad51, and with that for treatment of diseases associated with an abnormality of BRCA2-Rad51 complex formation and/or Rad51 action.

Growth Inhibition of Cancer Cells Using Contemplated Compounds

Figure 3:
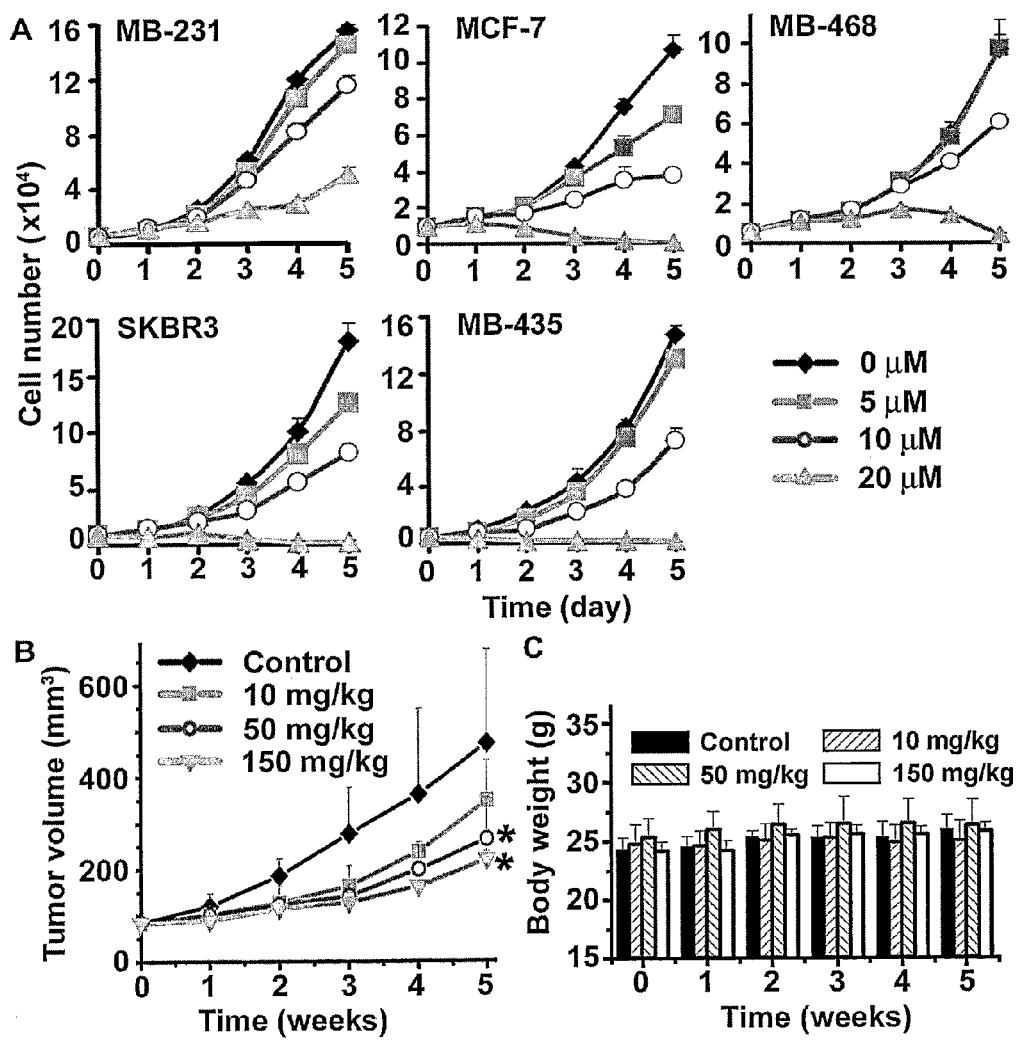
FIG. 3A is a series of graphs depicting effects of IBR2 on the growth of breast epithelial cell lines (MDA-MB-231, MCF-7, MDA-MB-468, SKBR3 and MDA-MB-435).
FIG. 3B is a graph depicting in vivo anti-tumor activity of IBR2 at various dosages on nude mice bearing human breast cancer xenograft (MDA-MB-468).
FIG. 3C is a graph depicting body weight of the animals used in the experiment of FIG. 3B.
FIG. 3D is a graph depicting $IC_{50}$ values of IBR2 for various cell lines.
FIG. 3E is a graph depicting proliferation of various cancer cell using IBR2 at various concentrations.
Figure 3D:
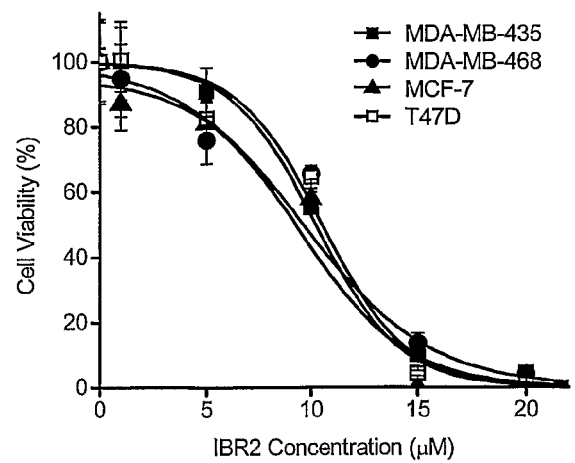
Figure 3E:
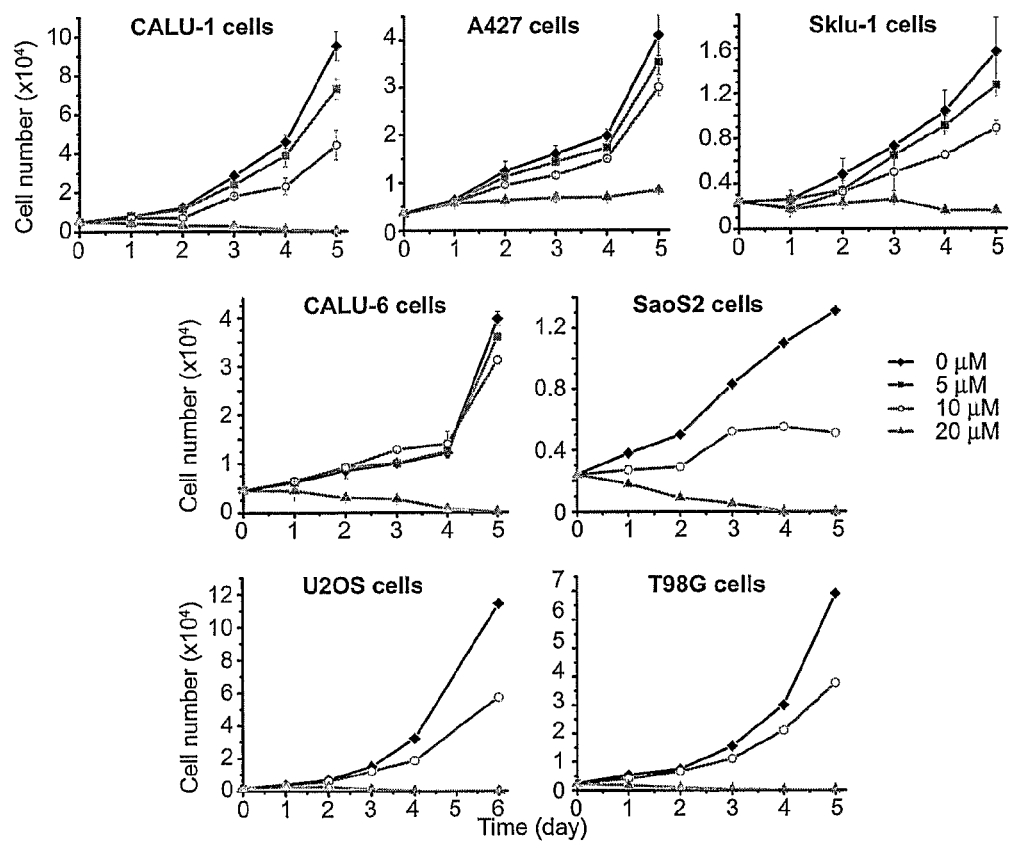

The inventors examined the effects of IBR2 on the growth and viability of a panel of breast cancer cell lines. Five exponentially growing breast cancer cell lines (MDA-MB-231, MCF-7, MDA-MB-468, SKBR3 and MDA-MB-435) were incubated with IBR2 at various concentrations (0, 5, 10 and 20 µM) for various periods of time (1, 2, 3, 4 and 5 days). The viable cell numbers were then counted by trypan blue exclusion assay. The results showed that IBR2 significantly inhibited the growth of all the five breast cancer cell lines in a dose- and time-dependent manner as depicted in FIG. 3A. We also examined the effects of IBR2 on the growth and viability of cultured breast cancer cells (MDA-MB-468, MDA-MB-435, MCF-7, T47D) using the 3-(4,5-dimethylthiazol-2-yl)-2,5-diphenyltetrazolium bromide (MTT) assay. The results showed that the IC50 values of IBR2 in the tested cell lines were about 10 µM (see FIG. 3D). Furthermore, proliferations of non-small-cell lung carcinoma cell lines (CALU-1, A427, Sklu-1 and CALU-6), osteosarcoma cell lines (SaoS2 and U2OS) and glioblastoma cell line (T98G) were also significantly inhibited by IBR2 treatment (see FIG. 3E).

To test the inhibitory effect of IBR2 on the growth of established tumor xenografts in nude mice, we chose the human breast cancer cell line MDA-MB-468 for this study. Mice with tumor size of approximately 85 mm3 were treated with three doses of IBR2 (10, 50 and 150 mg/kg i.p.) every other day for up to five weeks. Compared with the control group (vehicle alone), the IBR2 treated groups exhibited a significant retardation of tumor growth up to 65% in a dose-dependent manner (see FIG. 3B), while the average body weights of nude mice remained almost constant (see FIG. 3C). These results demonstrate that IBR2 can be used to inhibit breast tumor growth without apparent toxicity to animals.

Effect of IBR2 on Cell Cycle of MCF-7 Cells

Figure 4:
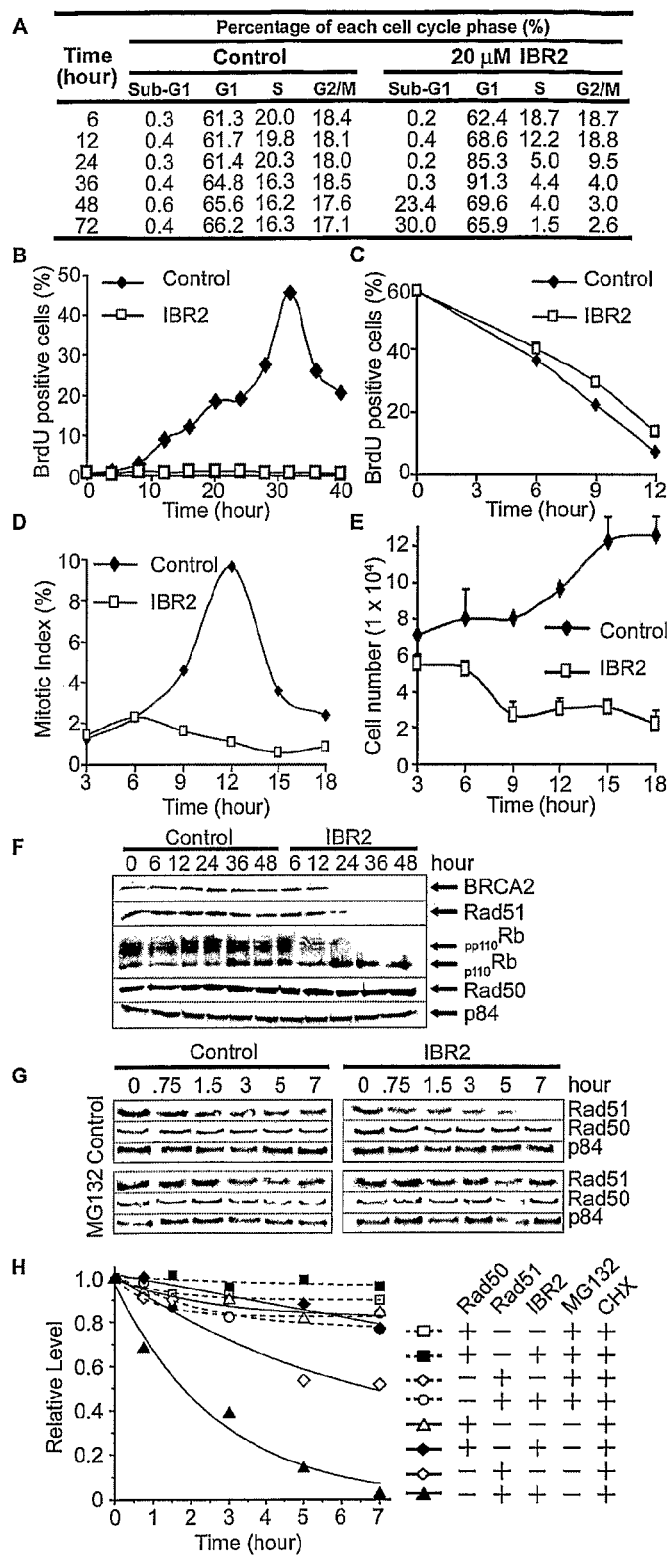
FIG. 4A is a table listing results of cell cycle distribution analysis by FACS for cells incubated with 20 μM IBR2 or DMSO.
FIG. 4B is a graph depicting percentage of BrdU positive cells treated with IBR2.
FIGS. 4C-4E are graphs depicting BrdU uptake (C), mitotic index (excluding prophase) (D), and the number of viable cells (E) of BrdU positive cells treated with IBR2.
FIGS. 4F and 4G are western blots depicting protein profiles of IBR2 treated cells.
FIG. 4H is a graph representing results from experiments of FIG. 4G.

To explore the mechanism of how IBR2 inhibits cancer cell growth, the inventors analyzed cell cycle progression of IBR2 treated MCF-7 cells by flow cytometry (FACS). As shown in FIG. 4A, in a time-dependent manner, the G1 fraction was increased, the S and G2/M fractions were depleted, and the sub-G1 fraction, indicative of apoptotic cells, was significantly increased.

To test whether IBR2 treated cells are arrested at G1 and thus fail to enter S phase, MCF-7 cells were synchronized at M phase by nocodazole treatment and then re-plated to allow the entry to G1 phase. At different time points, cells were pulse labeled with BrdU to monitor S phase entry. As shown in FIG. 4B, IBR2 treated cells were completely arrested at G1 and failed to enter S phase.

To further examine the fate of cells in S phase upon IBR2 treatment, MCF-7 cells were synchronized at G1/S transition by hydroxyurea treatment and then released to allow S phase entry by washing out the reagents. These cells were treated with 20 μM IBR2 and BrdU, and BrdU uptake was measured for DNA synthesis, as well as the mitotic index and the number of viable cells during an 18-hour period. As shown in FIG. 4C, the DNA syntheses in both mock and IBR2 treated cells were decreased at similar rates, suggesting that IBR2 treatment does not interfere with S phase progression. Mock treated cells reached M phase maximum at 12 hours, whereas no or little IBR2 treated cells entered M phase (FIG. 4D). Moreover, the number of mock treated cells doubled at the completion of M phase, while the number of IBR2 treated cells decreased to around 50%. This suggests that IBR2 treated S phase cells failed to enter M phase, probably due to the cell death at S/G2 phase (FIG. 4E).

To examine the impact of IBR2 on Rad51 protein expression, IBR2 treated MCF-7 cells was examined by straight western blot probed with a panel of antibodies against BRCA2, Rad51, Rad50, p84 and Rb. As shown in FIG. 4F, both BRCA2 and Rad51 decreased dramatically in a time dependent manner, while both p84 and Rad50 remained constant. Consistent with our FACS analysis (FIG. 4A), the hypophosphorylated form of Rb, a marker for G1 phase, was the major form observed in the later time points, further confirming that IBR2 arrests cells at G1 phase (FIG. 4A). It has been reported that BRCA2 level is cell cycle dependent, which expresses low in G1 phase and peaks at G1/S boundary. Therefore the decreased level of BRCA2 in IBR2 treated cells may be due to G1 phase arrest. Different from BRCA2 protein, Rad51 protein is expressed constant throughout the cell cycle in MCF-7 cells (data not shown). Therefore, loss of Rad51 protein may be the direct effect of IBR2 treatment instead of the consequence of G1 arrest. To test whether IBR2 decreases Rad51 levels by destabilization, the inventors performed a stability assay by adding cyclohexamide (CHX) to inhibit de novo protein synthesis. It was then observed that the half-life of Rad51, but not Rad50, was shortened to 1.5 hours compared with 5.5 hours in the control cells as evidenced in FIGS. 4G and 4H. With the addition of proteasome inhibitor MG132, the half-life of Rad51 was prolonged to the extent similar to that of Rad50 in both IBR2 treated and control cells (FIGS. 4G and 4H), suggesting that IBR2 targets Rad51 for proteasome-mediated degradation. Therefore, the inventors contemplate that IBR2 treated MCF-7 cells were arrested at G1, blocked at M phase entry, and died at S/G2 phase.

Effects of Contemplated Compounds on Rad51 and IR-Induced Rad51 Foci In Vivo Based on the observations presented herein, the inventors discovered that IBR2 binds Rad51 and disrupts the formation of BRCA2-Rad51 complex in vitro. In cells, IBR2 treatment leads to the degradation of Rad51, G1 arrest, and cell death at S phase. If the in vivo effects result from IBR2 targeting at Rad51, over-expression of exogenous Rad51 protein in IBR2 treated cells is expected to rescue such the effects. To test this possibility, the inventors expressed Rad51 with GFP as well as GFP alone in MCF-7 cells. Following treatment with IBR2, cells over-expressed Rad51 as can be taken from FIG. 5C and significantly rescued S phase entry based on BrdU uptake analysis as is evident from FIGS. 5A and 5B, which in turn suggests that Rad51 is specifically targeted by IBR2.

Next, the inventors examined the sensitivity to IBR2 treatment of isogenic MEFs with genotypes of BRCA2−/−: p53−/−, BRCA1−/−:p53−/− and p53−/−. BRCA2−/−:p53−/− MEFs were the most sensitive to IBR2 when compared with BRCA1−/−:p53−/− and p53−/− MEFs as can be taken from FIG. 5D. The stability of Rad51 protein was then compared in these MEFs, and it was found that the half-life of Rad51 in BRCA2−/−:p53−/− MEFs is shorter than the others (see FIG. 5E). These results suggest that endogenous BRCA2 may stabilize Rad51 by its association, while without BRCA2, Rad51 has a shortened half-life and is easily targeted for degradation by IBR2.

Figure 5:
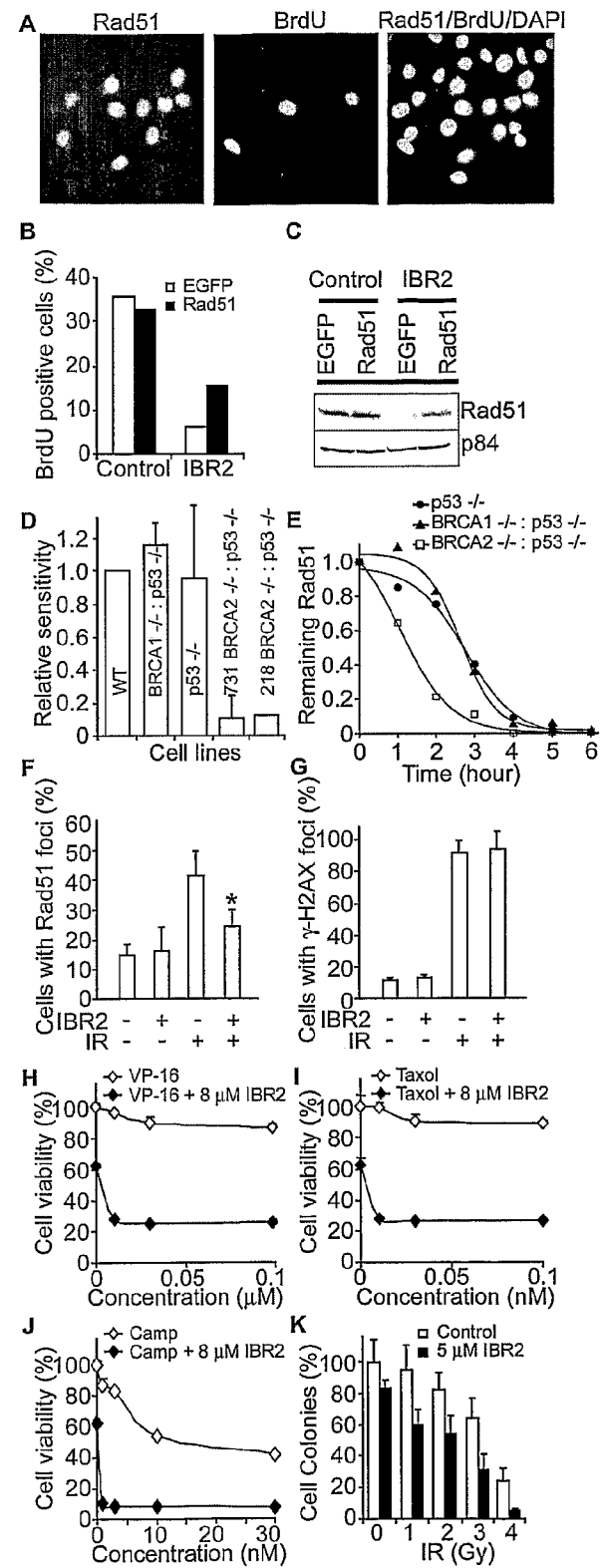
FIG. 5A are photomicrographs of IBR2 treated MCF-7 cells that overexpressed exogenous Rad51 to rescue S-phase entry.
FIG. 5B is a graph depicting BrdU positive cells expressed as a fraction of the total GFP expressing cells.
FIG. 5C is a western blot depicting expression level of Rad51.
FIG. 5D is a graph depicting relative sensitivities of selected cells lines.
FIG. 5E depicts remaining Rad51 quantities in selected cell lines.
FIG. 5F depicts number of cells with Rad51 foci in MCF-7 cells under selected treatment conditions.
FIG. 5G depicts number of cells with H2AX foci in MCF-7 cells under selected treatment conditions.
FIGS. 5H to 5J are graphs depicting synergistic effects of contemplated compounds with selected chemotherapeutic agents.
FIG. 5K is a graph depicting clonogenic survival of MCF-7 cells after γ-irradiation.

Since interaction between BRCA2 and Rad51 appears to be crucial for the formation of IR-induced Rad51 foci, it was contemplated that IBR2 may mimic BRC repeats to disrupt the BRCA2-Rad51 interaction and to thereby diminish the IR-induced Rad51 foci formation. To test this possibility, the number of the MCF-7 cells that formed IR-induced Rad51 foci was measured after IBR2 treatment. As shown in FIG. 5F, IBR2 treatment significantly reduced IR-induced Rad51 foci formation, suggesting that the double strand break (DSB) repair function of Rad51 was impaired by IBR2. To test whether this effect applies to other molecules involved in DSB repair, the inventors then examined the IR-induced foci formation of g-H2AX, which is histone H2AX phosphorylated at serine 139 by ATM for the recruitment of NBS1, 53BP and BRCA1, but not Rad51. As shown in FIG. 5G, IBR2 had no effect on g-H2AX foci formation upon IR treatment, suggesting that IBR2 specifically interferes with the Rad51 HR pathway without affecting the recruitment of g-H2AX to the DNA damage sites.

Synergy of Contemplated Compounds with Chemotherapeutic Agents

IBR2 apparently inhibits the function of Rad51 in cell cycle progression as well as in HR. It is therefore likely that combination of IBR2 with other chemotherapeutic agents may have synergistic effects. To test this possibility, survival of MCF-7 breast cancer cells treated with 8 μM IBR2 plus different doses of VP-16, taxol, camptothecin, or gamma-irradiation was measured. Significant synergistic effects of IBR2 were found with VP-16 (FIG. 5H), taxol (FIG. 5I), camptothecin (Camp) (FIG. 5J), and gamma-irradiation (FIG. 5K) on killing breast cancer cells. Thus, it should be appreciated that a combination of IBR2 with other conventional therapeutic agents may have potential clinical applications in treating various cancers.

Previous studies showed that cancer cells have higher S fraction than normal cells. This discrepancy is useful for developing many traditional drugs targeting to this property. An augmented expression level of Rad51 in many cancer cells was also observed. The significant difference of Rad51 function between cancer and normal cells may therefore provide a potential therapeutic window of Rad51 for cancer treatment. Consistently, contemplated compounds were able to retard tumor growth up to 65% at a dosage of 50 mg/kg, without apparent body weight loss up to a dosage of 150 mg/kg in our animal study. This result seems to confirm that contemplated compounds inhibit breast tumor growth while having little effect on somatic tissues and no apparent general toxicity. However, treatment with IBR alone may not be sufficient to eliminate cancer cells because IBR itself has little killing activity at G0/G1 phase. Thus, a combination with other chemotherapeutic agents may be necessary to achieve a better result. In this regard, co-treatment of IBR2 with other chemotherapeutic reagents, such as VP-16, taxol, and camptothecin, or ionizing irradiation may generate synergistic effects, suggesting the compounds can be used as a sensitizer of conventional chemo- or radio-therapies.

The absence of BRCA2 in cells also appears to have a significant impact on Rad51 stability rendering them much more sensitive to IBR2 treatment. Consistently, preliminary results indicate that a pancreatic cancer cell line, CAPAN-1, which contains a truncated BRCA2, showed a significant sensitivity to IBR2. It is therefore contemplated that IBR2 may be particularly useful in treating cancer cells lacking functional BRCA2 (or having a reduced BRCA2 expression) albeit only a small fraction of cancer.

Experimental Procedures

Reverse Yeast Two-hybrid Screening: The chemical library was purchased from Nanosyn, Inc. (Menlo Park, Calif.). TetR/NCB which contains BRC1-4 repeats was expressed constitutively; the expression of AD/Rad51 was galactose-inducible under GAL1 promoter. Yeast was grown in a galactose medium containing 5-FOA. The assay was performed on 96-well plates with 10 μM compounds in 100 μl total volume. Compounds that can disrupt the BRC-Rad51 interaction were identified by the viability of the yeast.

Molecular modeling: IBR2 structure was generated with Sybyl (Tripos co. ltd.), and charges were added using Gasteiger-Huckel method (Gasteiger and Marsili, 1980). Molecular docking was conducted using UCSF Dock (Ewing and Kuntz, 1997) by flexible docking method, and the results were viewed with Chimera (Huang et al., 1996). Rad51 and BRC4 coordinates were from PDB (Accession No: 1N0W). Rad51 oligomerization motif coordinates were from PDB (Accession No: 1PZN). For 3D structure alignment, IBR2 coordinates were from one of the docked conformations.

Surface Plasmon Resonance binding assays: The assays were performed at 25° C. in HBSD buffer (10 mM HEPES, 150 mM NaCl, 0.1% DMSO) on Biacore3000 (Biacore Inc.). Sensor chips NTA or glutathione-modified CM5 were used to capture His-Rad51 or GST-BRC1, respectively. The capture level was about 130 resonance units at a flow rate of 5 μl/min. For sequential binding assays, chips were treated with compounds (1 μM) and then proteins (50 μg/ml). The retained resonance units (RU) were recorded and averaged from triplicate experiments. For competition assays (Vassilev et al., 2004), IBR2 was incubated with 50 μg/ml BRC at 25° C. for 15 minutes prior to use. Relative binding percentages were calculated with respect to the binding without IBR2 and averaged from two independent experiments.

Gel filtration: A mixture of Rad51 (3.2 μg) and small compound (molar ratio 1:10) was incubated for 15 minutes at 37° C., supplemented with buffer (50 mM triethanolamine-HCl [pH 7.5], 0.5 mM Mg (OAc)2, 1 mM dithiothreitol, 2 mM ATP, and 100 μg/ml BSA, total volume 20 μl) and incubated 15 more minutes. Then the mixture was loaded onto 2.4 ml Superdex 200 PC 3.2/30 columns (Pharmacia) equilibrated with the same buffer as described (Davies et al., 2001). Fractions (50 μl) were collected and 0.5 μl of each fraction was blotted onto PVDF membrane. Rad51 was detected using anti-Rad51 antibody (mAb 14B4).

Cell culture, cell synchronization, BrdU labeling and determination of mitotic index: Breast cancer cell lines and MEF cell lines were cultured in high-glucose Dulbecco modified Eagle medium containing 10% fetal bovine serum. MCF-10A cells were cultured as described previously (Debnath et al., 2003). Cell synchronization at M phase was achieved by treatment with 0.1 μg/ml nocodazole for 8 hours. Cell synchronization at G1/S boundary was achieved by treatment with 1 mM hydroxyurea for 17 hours, 9 hours of release and again with 1 mM hydroxyurea for 14 hours. For BrdU labeling, cells were incubated with BrdU for 30 minutes and fixed for BrdU immunostaining using a BrdU labeling kit (Amersham Biosciences). For determination of mitotic index, cells were fixed in 4% formaldehyde in PBS containing 0.1 μg/ml DAPI for 30 minutes at room temperature and examined by fluorescence microscopy. 500-1000 nuclei per sample were counted to determine the number of M phase cells which only includes prometaphase, metaphase, anaphase and telophase.

Cell proliferation assay and clonogenic survival assays: To obtain cell growth curves, $1 \times 10^4$ cells were seeded in 12-well plate for 24 hours. Cells were then treated, in duplicate, with various concentrations of IBR2 in the presence of 0.4% DMSO. The viable cells were counted by trypan blue exclusion assay daily. MTT assay was performed as previously described (Alley et al., 1988).

To perform clonogenic survival assay, $1.5 \times 10^3$ MCF-7 cells were seeded in 10-cm dishes for 24 hours. Cells were then treated, in triplicate, with 5 μM IBR2 for 12 hours and then g-irradiated. Cells were continuously exposed to 5 μM IBR2 and re-fed every 4 days with fresh medium and IBR2. After 14-16 days, cells were fixed and stained with 2% methylene blue. Colonies consisting of more than 50 cells were counted.

Western blot analysis: Cells were treated with 20 mM IBR2 or 50 μg/ml cycloheximide (CHX) or 1 μM MG132 and harvested at different time points for western blot analysis. Cells resuspended in Lysis 250 buffer were subjected to three freeze/thaw cycles (liquid nitrogen/37° C.) and then centrifuged at 14,000 rpm for 2 minutes at room temperature. After measuring protein concentration, equal amount of total cellular proteins were subjected to SDS-PAGE and immunoblot analyses were performed as described previously (Chen et al., 1999). Antibodies used were: Rad51 (rabbit 5952); BRCA2 (rabbit PC146, Oncogene); Rb (mAb 11D7); Rad50 (mAb 13B3) and p84 (mAb 5E10). The intensity of bands was quantified by densitometry using Labworks 4.5 software. The relative value of the band intensity was calculated with respect to that of untreated sample after normalization with the p84 signal.

Immunostaining Rad51 and g-H2AX foci: MCF-7 cells were treated with 20 μM IBR2 for 7 or 19 hours and then g-irradiated at 20 Gy. Cells were incubated for an additional 5 hours with 20 μM IBR2, then fixed with 4% paraformaldehyde in PBS containing 0.5% Triton X-100. The fixed cells were incubated with a-Rad51 antibody (mAb 1F5) or a-g-H2AX antibody (Upstate). Rad51 and g-H2AX foci positive cells were subsequently counted as described (Chen et al., 1999).

Cell cycle analysis by flow cytometry: To analyze cell cycle distribution, $5'10^5$ MCF-7 cells were seeded in 10-cm dishes for 24 hours and treated with 20 mM IBR2 for various times. Cells were then trypsinized and fixed with 70% ethanol (−20° C.) and stained for 30 minutes with propidium iodide (PI) staining solution (Yun et al., 2005) (50 μg/ml PI, 0.1% sodium citrate, 50 μg/ml RNase A, 0.03% NP-40 in PBS). Flow cytometry analysis was performed using a FACScalibur flow cytometer and cell cycle distribution was analyzed with CellQuest software (Beckton Dickison). 10,000 events were analyzed for each sample and the experiment was repeated twice.

Construct and overexpression of Rad51 protein in MCF-7 cells: Rad51-EGFP was generated by inserting a 1.1 kb Rad51 fragment into a retroviral vector pCLpGKEGFP. Rad51-EGFP retrovirus were then produced and infected into MCF-7 cells. Cells stably infected with Rad51-EGFP were treated with 20 μM IBR2 for 24 hours then labeled with BrdU or lysed for Western blot analysis.

Tumor inhibition assay in nude mice: $5 \times 10^6$ MDA-MB-468 cells in 100 μl of PBS were injected into mammary fat pad of 6-8 week old athymic female BALB/c-nude mice (nu/nu) (Charles River Laboratories). After tumors grew to 85 $mm^3$ (day 12), mice were randomized into four groups (n=5 per group) to receive intraperitoneal injection of IBR2 (10, 50, or 150 mg/kg) or vehicle (15% DMSO, 20% Tween 20, 10% PEG400, 55% saline) every other day for 5 weeks. Body weights of mice and tumor volumes were measured twice weekly during the course of drug treatment. A Student's t test was used to determine P value.

Thus, specific embodiments and applications of compositions and methods for disruption of BRCA2-Rad51 interaction have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Furthermore, where a definition or use of a term in a reference, which is incorporated by reference herein is inconsistent or contrary to the definition of that term provided herein, the definition of that term provided herein applies and the definition of that term in the reference does not apply.

What is claimed is:

1. A pharmaceutical composition comprising a pharmaceutically acceptable carrier and a compound according to Formula 1

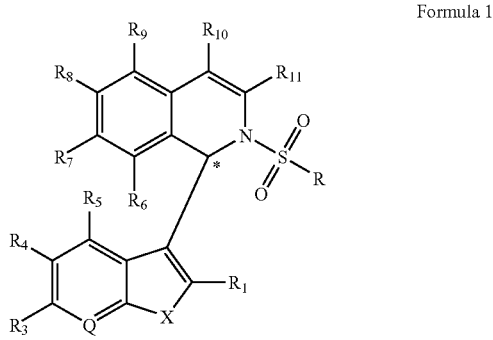

Formula 1 wherein R is a radical selected from the group consisting of an alkenyl, alkynyl, benzyl, and

wherein Y is an alkylene group having 1 to 4 carbon atoms; Z is selected from —CH=N—, —N=CH—, O, S, or $NR_{14}$, where $R_{14}$ is H, alkyl, aryl, alkaryl, or acyl;

Q is N or C—$R_2$
X is selected from $CH_2$, O, S, or $NR_{14}$, where $R_{14}$ is independently as defined above;
R' and $R_1$ through $R_{11}$ are independently selected from the group consisting of H, alkyl, alkenyl, alkynyl, cycloalkyl, cycloalkenyl, halo, nitro, hydroxy, alkoxy, alkenyloxy, cyano, carboxy, alkoxycarbonyl, carboxyalkyl, amino, acylamino, alkylamino, dialkylamino, cycloalkylamino, N-alkyl, N-cycloalkyl, amino, thio, alkylthio, and haloalkyl; and
wherein n is between 0 and 4, inclusive, and wherein * denotes R or S configuration.

2. The pharmaceutical composition of claim 1 wherein $R_1$ through $R_{11}$ are H, wherein X is $NR_{14}$, and wherein R is

3. The pharmaceutical composition of claim 1 wherein the compound has a structure according to Formula 3

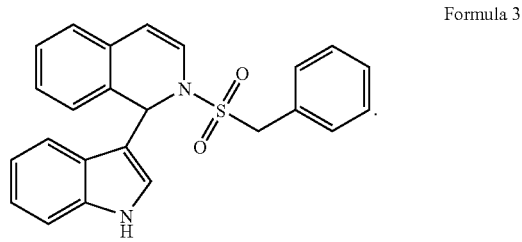

Formula 3

4. The pharmaceutical composition of claim 1 wherein the compound is present in the composition at a concentration effective to increase sensitivity of a neoplastic cell to at least one of radiation and a DNA-damaging agent when the cell is exposed to the compound.

5. The pharmaceutical composition of claim 1 wherein the compound is present in the composition at a concentration effective to reduce binding of BRCA2 to RAD51 when a BRCA2-RAD51 complex is exposed to the compound.

6. The pharmaceutical composition of claim 1 further comprising a DNA-damaging agent.

7. The pharmaceutical composition of claim 1 wherein the compound is present in the composition at a concentration effective to arrest a cell in G1 phase when the cell is contacted with the compound.

8. The pharmaceutical composition of claim 1 wherein the compound is coupled to an implanted device at a concentration effective to reduce cell proliferation of a plurality of cells proximal to the implanted device.

* * * * *